US010925823B2

(12) United States Patent
Schwartz et al.

(10) Patent No.: US 10,925,823 B2
(45) Date of Patent: Feb. 23, 2021

(54) SYNERGISTIC ANTIOXIDANT COMPOSITIONS

(71) Applicant: The Procter & Gamble Company, Cincinnati, OH (US)

(72) Inventors: James Robert Schwartz, Cincinnati, OH (US); Leo Timothy Laughlin, II, Mason, OH (US); Lijuan Li, Lebanon, OH (US); Junjun Chen, Mason, OH (US); Kathleen Marie Kerr, Okeana, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

(21) Appl. No.: 16/412,745

(22) Filed: May 15, 2019

(65) Prior Publication Data
US 2019/0350831 A1 Nov. 21, 2019

Related U.S. Application Data

(60) Provisional application No. 62/671,639, filed on May 15, 2018.

(51) Int. Cl.
| *A61K 8/00* | (2006.01) |
| *A61K 8/49* | (2006.01) |
| *A61P 39/06* | (2006.01) |
| *A61K 8/27* | (2006.01) |
| *A61K 9/00* | (2006.01) |
| *A61Q 5/00* | (2006.01) |
| *A61Q 5/02* | (2006.01) |
| *A61Q 5/12* | (2006.01) |

(52) U.S. Cl.
CPC ............. *A61K 8/4933* (2013.01); *A61K 8/27* (2013.01); *A61K 8/4926* (2013.01); *A61K 9/0014* (2013.01); *A61P 39/06* (2018.01); *A61Q 5/006* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| 4,796,812 | A | 1/1989 | Grollier |
| 6,060,044 | A | 5/2000 | Cretois |
| 8,360,973 | B2 | 1/2013 | Bazin |
| 9,996,674 | B2 | 6/2018 | Segman |
| 10,543,157 | B2 * | 1/2020 | Davis ................ A61K 8/4926 |
| 2002/0150287 | A1 | 10/2002 | Kobayashi |
| 2002/0183988 | A1 | 12/2002 | Skaanning |
| 2003/0215522 | A1 | 11/2003 | Johnson |
| 2004/0213751 | A1 | 10/2004 | Schwartz |
| 2009/0274642 | A1 | 11/2009 | Dawson, Jr. |
| 2010/0106679 | A1 | 4/2010 | Yamaguchi |
| 2012/0309733 | A1 | 12/2012 | Chang et al. |
| 2014/0028822 | A1 | 1/2014 | Khadavi |
| 2014/0071456 | A1 | 3/2014 | Podoleanu et al. |
| 2014/0120048 | A1 | 5/2014 | Krueger |
| 2014/0171471 | A1 | 6/2014 | Krueger |
| 2014/0378810 | A1 | 12/2014 | Davis |
| 2015/0217465 | A1 | 8/2015 | Krenik |
| 2015/0272865 | A1 | 10/2015 | Mette |
| 2016/0038397 | A1 | 2/2016 | Markland |
| 2016/0310393 | A1 | 10/2016 | Chang |
| 2016/0346184 | A1 | 12/2016 | Schwartz |
| 2017/0135932 | A1 | 5/2017 | Schwartz |
| 2017/0270593 | A1 | 9/2017 | Sherman |
| 2017/0367963 | A1 | 12/2017 | Kadir |
| 2018/0040052 | A1 | 2/2018 | Robinson |
| 2018/0225673 | A1 | 8/2018 | Dubey |
| 2018/0325791 | A1 | 11/2018 | Lane |
| 2019/0035149 | A1 | 1/2019 | Chen |
| 2019/0350514 | A1 | 11/2019 | Purwar |
| 2019/0350819 | A1 | 11/2019 | Hamersky |
| 2019/0355115 | A1 | 11/2019 | Niebauer |
| 2020/0214953 | A1 | 7/2020 | Lane |

FOREIGN PATENT DOCUMENTS

| DE | 102012203240 A1 | 3/2013 |
| DE | 202015002188 U1 | 5/2015 |
| WO | WO9939683 A1 | 8/1999 |
| WO | WO2012058557 A2 | 5/2012 |
| WO | WO2014073456 A1 | 5/2014 |
| WO | WO2014208162 A1 | 12/2014 |

OTHER PUBLICATIONS

"Anti-Dandruff Treatment Hair Cream", Mintel, Sep. 3, 2018.
"Balancing and Anti-Dandruff Shampoo", Mintel, Jan. 6, 2014.
"Double Care Anti-Dandruff Treatment Hair Cream", Mintel, Oct. 16, 2012.
"Hair Lotion", Mintel, Oct. 7, 2019.
"Moist-Up Eye Cream", Mintel, Nov. 11, 2009.
"Moisturizing Anti-Dandruff Shampoo", Mintel, Mar. 17, 2016.
All final and non-final office actions for U.S. Appl. No. 15/976,485 (P&G Case 14812).
All final and non-final office actions for U.S. Appl. No. 16/441,749 (P&G Case AA1288MC).
All final and non-final office actions for U.S. Appl. No. 16/413,920 (P&G Case 15229).
PCT International Search Report and Written Opinion for PC/US2018/032046 dated Jun. 27, 2018.

(Continued)

*Primary Examiner* — Susan T Tran
(74) *Attorney, Agent, or Firm* — Linda M. Sivik

(57) ABSTRACT

The present invention discloses to a personal care composition having a polyvalent metal salt of pyrithione; a 2-pyridinol-N-oxide material; and a zinc containing layered material; wherein the ratio of a:b is from about 0.5 to about 1.5; the ratio of b:c is about 0.2 to about 1.0; and the ratio of a:c is about 0.2 to about 1.0 and wherein there is a synergistic antioxidant activity.

16 Claims, 5 Drawing Sheets

(56) References Cited

OTHER PUBLICATIONS

PCT International Search Report and Written Opinion for PCT/US2019/032382 dated Jul. 31, 2019.
PCT International Search Report and Written Opinion for PCT/US2019/032402 dated Aug. 28, 2019.
PCT International Search Report and Written Opinion for PCT/US2019/032404 dated Jul. 30, 2019.
PCT International Search Report and Written Opinion for PCT/US2019/066785 dated Mar. 26, 2020.
Schwartz, J.R. et al., "The role of oxidative damage in poor scalp health: ramifications to causality and associated hair growth", International Journal of Cosmetic Science, vol. 37, No. Suppl. 2, Sp. Iss. SI, Dec. 2015, pp. 9-15.

* cited by examiner

SYNERGISTIC ANTIOXIDANT COMPOSITIONS

FIELD OF THE INVENTION

The present invention relates to personal care compositions comprising a polyvalent metal salt of pyrithione, a 2-pyridinol-N-oxide material and a zinc containing layered material demonstrating synergistic antioxidant activity.

BACKGROUND OF THE INVENTION

The skin is a complex organ in which the overall condition is directly impacted by the oxidative balance. There are many endogenous and exogenous sources of oxidizing species which the skin attempts to counteract with a series of endogenous antioxidant enzymes (such as superoxide dismutase). When the level of oxidizing species is greater than can be counteracted by the skin, the imbalance is called oxidative stress. There are numerous detrimental effects of oxidative stress, such as oxidized lipids and proteins that lead to compromised skin function, such as decreased barrier effectiveness. This can lead to skin dryness, excessive flaking and itch and prevent hair loss.

The sources of oxidative stress include those of exogenous origin such as pollutions, cigarette smoke, ultraviolet light and certain product exposures. Sources of endogenous reactive oxygen species (ROS) include the effects of aging as well as those originating from microbial metabolism. The scalp is an especially susceptible portion of the skin. *Malassezia* fungi are a known source of ROS. Ultraviolet light exposure is also difficult to avoid on the scalp.

Antioxidants are materials that can supplement the body's ability to defend against ROS species. These beneficial agents can be delivered orally or topically. For skin benefits, direct topical delivery is desired.

Between increasing environmental ROS sources and decreasing ability to counteract them in an aging population, there is a need for more effective topically delivered antioxidant materials. While there is a wide range of individual antioxidants available, unique combinations have the potential to result in synergistic activities, wherein the delivered activity is more than the sum of individual components. Binary synergies are challenging to identify, ternary synergies are even more unique. Such combinations are especially useful to supplement the body's native antioxidant activity.

SUMMARY OF THE INVENTION

The present invention is directed to a personal care composition comprising a polyvalent metal salt of pyrithione; a 2-pyridinol-N-oxide material; and a zinc containing layered material; wherein the ratio of a:b is from about 0.5 to about 1.5; the ratio of b:c is about 0.2 to about 1.0; and the ratio of a:c is about 0.2 to about 1.0 and wherein there is a synergistic antioxidant activity.

DETAILED DESCRIPTION OF THE INVENTION

Figure 1:
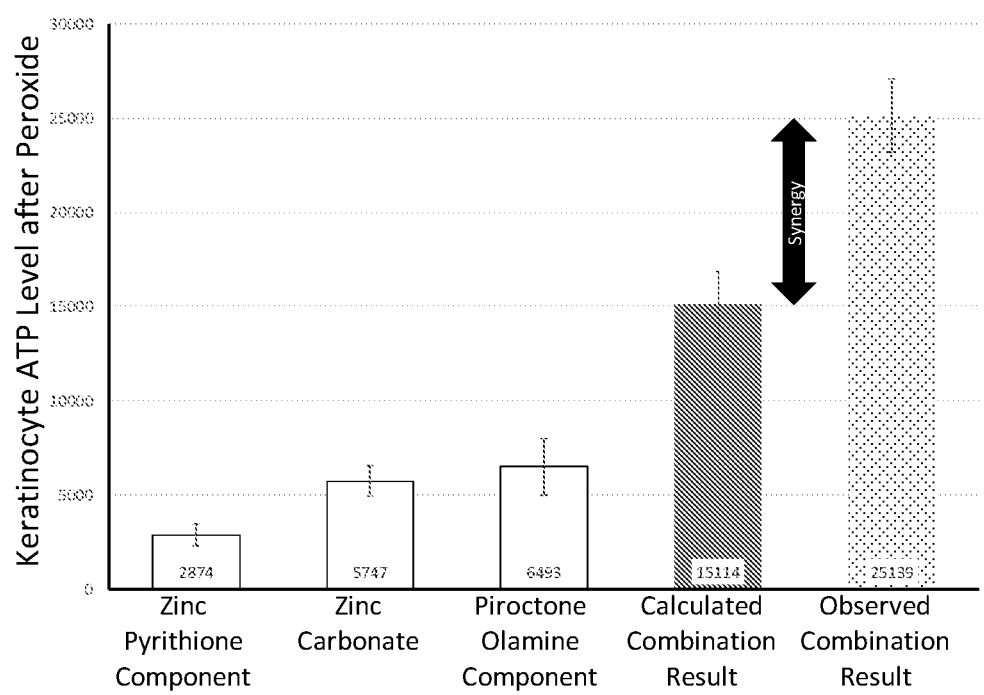
FIG. 1 depicts a Peroxide-Induced Keratinocyte Stress assay demonstrating a statistically significant (p=0.0003) synergistic level of activity for the triad over the calculated sum of individual observations.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

As used herein, "comprising" means that other steps and other ingredients which do not affect the end result can be added. This term encompasses the terms "consisting of" and "consisting essentially of".

As used herein, "mixtures" is meant to include a simple combination of materials and any compounds that may result from their combination.

As used herein, "molecular weight" or "Molecular weight" refers to the weight average molecular weight unless otherwise stated. Molecular weight is measured using industry standard method, gel permeation chromatography ("GPC").

Synergy is defined as occurring when two or more substances produce a combined effect greater than the sum of their separate effects. Binary synergies involve two components whereas ternary synergies involve three components.

Where amount ranges are given, these are to be understood as being the total amount of said ingredient in the composition, or where more than one species fall within the scope of the ingredient definition, the total amount of all ingredients fitting that definition, in the composition. All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Unless otherwise noted, all component or composition levels are in reference to the active portion of that component or composition, and are exclusive of impurities, for example, residual solvents or by-products, which may be present in commercially available sources of such components or compositions.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

1. Pyridinethione Salts

Pyridinethione scalp health agent particulates, especially 1-hydroxy-2-pyridinethione salts, are one type of a particulate scalp health agent for use in compositions of the present invention. The concentration of pyridinethione scalp health agent particulate typically ranges from about 0.05% to about 5%, by weight of the composition, further the concentration of scalp health agent ranges from about 0.1% to about 3%, by weight of the composition, or from about 0.1% to about 2%. In another aspect of the present invention, pyridinethione salts include those formed from heavy metals such as zinc, copper, tin, cadmium, magnesium, aluminum and zirconium. The present invention may have a pyridinethione salts formed from a heavy metal zinc, and further may have the zinc salt of 1-hydroxy-2-pyridinethione (known as "zinc pyridinethione" or "ZPT"), and yet further may have 1-hydroxy-2-pyridinethione salts in platelet particle form, wherein the particles have an average size of up to about 20μ. The present invention may have the particles having an average size up to about 5μ, and further up to about 2.5μ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the scalp health agent particulate in the compositions herein, that the growth or re-growth of hair may be stimulated or regulated, or both, or that hair loss may be reduced or inhibited, or that hair may appear thicker or fuller.

Zinc-Containing Layered Material

The composition comprises an effective amount of a zinc-containing layered material. Zinc-containing layered materials may be those with crystal growth primarily occurring in two dimensions. It is conventional to describe layer structures not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. The ZLM may be selected from the group consisting of: hydrozincite (zinc carbonate hydroxide), basic zinc carbonate, aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. The ZLM may be a layered double hydroxide conforming to the formula $[M^{2+}_{1-x}M^{3+}_x(OH)_2]^{x+} A^{n-}_{x/m} \cdot nH_2O$ wherein some or all of the divalent ions ($M^{2+}$) are zinc ions (Crepaldi, E L, Pava, P C, Tronto, J, Valim, J B J. Colloid Interfac. Sci. 2002, 248, 429-42).

Yet another class of ZLMs can be prepared called hydroxy double salts (Morioka, H., Tagaya, H., Karasu, M, Kadokawa, J, Chiba, K Inorg. Chem. 1999, 38, 4211-6). The ZLM may be a hydroxy double salt conforming to the formula $[M^{2+}_{1-x}M^{2+}_{1+x}(OH)_{3(1-y)}]^+ A^{n-}_{(1=3y)/n} \cdot nH_2O$ where the two metal ions ($M^{2+}$) may be the same or different. If they are the same and represented by zinc, the formula simplifies to $[Zn_{1+x}(OH)_2]^{2x+} 2xA^- \cdot nH_2O$. This latter formula represents (where x=0.4) materials such as zinc hydroxychloride and zinc hydroxynitrate. The ZLM may be zinc hydroxychloride and/or zinc hydroxynitrate. These are related to hydrozincite as well wherein a divalent anion replace the monovalent anion. These materials can also be formed in situ in a composition or in or during a production process.

The composition of the present invention may comprise basic zinc carbonate. Commercially available sources of basic zinc carbonate include Zinc Carbonate Basic (Cater Chemicals: Bensenville, Ill., USA), Zinc Carbonate (Shepherd Chemicals: Norwood, Ohio, USA), Zinc Carbonate (CPS Union Corp.: New York, N.Y., USA), Zinc Carbonate (Elementis Pigments: Durham, UK), and Zinc Carbonate AC (Bruggemann Chemical: Newtown Square, Pa., USA). Basic zinc carbonate, which also may be referred to commercially as "Zinc Carbonate" or "Zinc Carbonate Basic" or "Zinc Hydroxy Carbonate", is a synthetic version consisting of materials similar to naturally occurring hydrozincite. The idealized stoichiometry is represented by $Zn_5(OH)_6(CO_3)_2$ but the actual stoichiometric ratios can vary slightly and other impurities may be incorporated in the crystal lattice.

The composition of the present invention may comprise an effective amount of a zinc-containing layered material. The composition of the present invention may comprise from about 0.001% to about 10%, or from about 0.01% to about 7%, or from about 0.1% to about 5% of a zinc-containing layered material, by total weight of the composition.

2-Pyridinol-N-Oxide Materials

2-Pyridinol-N-oxide materials suitable for use in this invention include a substituted or unsubstituted 2-pyridinol-N-oxide material or a salt thereof. Included within the scope of this invention are tautomers of this material, e.g., 1-hydroxy-2(1H)-pyridinone. The substituted or unsubstituted 2-pyridinol-N-oxide material and its corresponding tautomeric form, 1-hydroxy-2(1H)-pyridinone, are shown below:

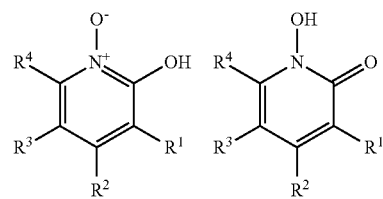

where $R^1$, $R^2$, $R^3$, $R^4$ groups are independently selected from the group consisting of H, Cl, Br, I, F, NO, $NO_2$, and $(CH_2)_n G$, where each G is independently selected from the group consisting of $(O)_m SO_3 M^3$, $(O)_m CO_2 M^3$, $(O)_m C(O)(R^5)$, $(O)_m C(O)N(R^5 R^6)$, $(O)_m CN$, $(O)_m (R^5)$, and $N(R^5 R^6)$, where m is 0 or 1, n is an integer from 0 to 4, $R^5$ and $R^6$ are independently selected from the group consisting of H and a substituted or unsubstituted $C_1$-$C_{12}$ organic group, and $M^3$ is selected from the group consisting of H, a substituted or unsubstituted $C_1$-$C_{12}$ organic group, $+N(R^7R^8R^9R^{10})$, and $1/q\ M'^{q+}$ where M' is selected from the group consisting of an alkali metal of charge q and an alkaline earth metal of charge q, where $R^7$, $R^8$, $R^9$, and $R^{10}$ are independently selected from the group consisting of H and a substituted or unsubstituted $C_1$-$C_{12}$ organic group, and where any pair of vicinal groups, $R^1$ and $R^2$, $R^2$ and $R^3$, $R^3$ and $R^4$ may be taken together to form another five- or six-membered aromatic or aliphatic ring optionally substituted with one or more groups selected from the group consisting of Cl, Br, I, F, NO, $NO_2$, CN, $(CH_2)_nG$, and mixtures thereof. Suitable organic groups include $(C_1$-$C_{12})$alkyl, $(C_2$-$C_{12})$alkenyl, and $(C_2$-$C_{12})$alkynyl. The organic group may optionally be substituted and suitable substituent groups include a hydroxyl group, a carboxyl group, and an amino group. 2-pyridinol-N-oxide is also known, for example, as 2-hydroxypyridine-N-oxide, 2-pyridinol-1-oxide, or 2-hydroxypyridine-1-oxide.

In certain aspects, the 2-pyridinol-N-oxide material is a 2-pyridinol-N-oxide material or tautomer thereof according to the formula(s) above, where $R^1$, $R^2$, $R^3$, $R^4$ are independently selected from the group consisting of H, Cl, and $(CH_2)_nG$, where G is independently selected from the group consisting of $(O)_mSO_3M^3$, $(O)_mCO_2M^3$, $(O)_mC(O)(R^5)$, $(O)_mCN$, and $(O)_m(R^5)$, where m is 0 or 1. In other aspects, the 2-pyridinol-N-oxide material is a 2-pyridinol-N-oxide material according to the formula above, where $R^1$, $R^2$, $R^3$, $R^4$ are independently selected from the group consisting of H, $SO_3M^3$, and $CO_2M^3$. In still other aspects, $R^1$, $R^2$, $R^3$, $R^4$ are independently selected from the group consisting of H, $SO_3M^3$, and $CO_2M^3$, where no more than one $R^1$, $R^2$, $R^3$, $R^4$ is $SO_3M^3$ or $CO_2M^3$.

In certain aspects, the 2-pyridinol-N-oxide material is the salt of a substituted or unsubstituted 2-pyridinol-N-oxide material. In these aspects, the hydrogen of the hydroxyl group of the 2-pyridinol-N-oxide material may be substituted with a suitable charge-balancing cation. In these aspects, non-limiting examples of the hydrogen-substituting cation include $Na^+$, $Li^+$, $K^+$, $½ Mg^{2+}$, or $½ Ca^{2+}$, substituted ammonium, such as $C_1$-$C_6$ alkanolammnonium, mono-ethanolamine (MEA), tri-ethanolamine (TEA), di-ethanolamine (DEA), or any mixture thereof. In some aspects, in solution, the cation may be dissociated from the 2-pyridinol-N-oxide or the 1-hydroxy-2(1H)-pyridinone anion.

In certain aspects, the 2-pyridinol-N-oxide material is of a substituted or unsubstituted 2-pyridinol-N-oxide material. Salts for use herein include those formed from the polyvalent metals barium, bismuth, strontium, copper, zinc, cadmium, zirconium and mixtures thereof.

In some aspects, the 2-pyridinol-N-oxide material is selected from the group consisting of: 6-hydroxy-3-pyridinesulfonic acid, 1-oxide (CAS 191672-18-1); 2-hydroxypyridine-1-oxide (CAS 13161-30-3); 2-hydroxy-4-pyridinecarboxylic acid, 1-oxide (CAS 13602-64-7); 5-ethoxy-2-pyridinol, 2-acetate, 1-oxide (CAS 51984-49-7); 1-(3-hydroxy-2-oxido-4-isoquinolinyl)-ethanone (CAS 65417-65-4); 6-hydroxy-3-pyridinecarboxylic acid, 1-oxide (CAS 90037-89-1); 2-methoxy-4-quinolinecarbonitrile, 1-oxide (CAS 379722-76-6); 2-pyridinecarboxylic acid, 6-hydroxy-, 1-oxide (CAS 1094194-45-2); 3-pyridinecarboxylic acid, 2-hydroxy-, 1-oxide (CAS 408538-43-2); 2-pyridinol, 3-nitro-, 1-oxide (CAS 282102-08-3); 3-pyridinepropanenitrile, 2-hydroxy-, 1-oxide (193605-60-6); 3-pyridineethanol, 2-hydroxy-, 3-acetate, 1-oxide (CAS 193605-56-0); 2-pyridinol, 4-bromo-, 1-oxide (CAS 170875-41-9); 2-pyridinol, 4,6-dibromo-, 2-acetate, 1-oxide (CAS 170875-40-8); 2-pyridinol, 4,6-dibromo, 1-oxide (CAS 170875-38-4); 2-pyridinol, 4-(2-aminoethyl)-, 1-oxide (CAS 154403-93-7); 2-pyridinol, 5-(2-aminoethyl)-, 1-oxide (CAS 154403-92-6); 3-pyridinepropanoic acid, α-amino-6-hydroxy-, 1-oxide (CAS 134419-61-7); 2-pyridinol, 3,5-dimethyl, 1-oxide (CAS 102074-62-4); 2-pyridinol, 3-methyl-, 1-oxide (CAS 99969-07-0); 2-pyridinol, 3,5-dinitro, 1-oxide (CAS 98136-47-1); 2-pyridinol, 3,5-dibromo-, 1-oxide (CAS 98136-29-9); 2-pyridinol, 4-methyl-6-(2-methylpropyl)-, 1-oxide (CAS 91408-77-4); 2-pyridinol, 3-bromo-4,6-dimethyl-, 1-oxide (CAS 91408-76-3); 2-pyridinol, 4,5,6-trimethyl-, 1-oxide (CAS 91408-75-2); 2-pyridinol, 6-heptyl-4-methyl-, 1-oxide (CAS 91408-73-0); 2-pyridinol, 6-(cyclohexylmethyl)-4-methyl-, 1-oxide (CAS 91408-72-9); 2-pyridinol, 6-bromo-, 1-oxide (CAS 89284-00-4); 2-pyridinol, 5-bromo-, 1-oxide (CAS 89283-99-8); 2-pyridinol, 3,5-dichloro-4,6-difluoro-, 1-oxide (CAS 33693-37-7); 2-pyridinol, 3,4,5,6-tetrachloro-, 1-oxide (CAS 32835-63-5); 2-pyridinol, 6-methyl-, 1-oxide (CAS 14420-62-3); 2-pyridinol, 5-nitro-, 1-oxide (CAS 14396-03-3); 2-pyridinol, 4-methyl-5-nitro-, 1-oxide (CAS 13602-77-2); 2-pyridinol, 4-chloro-5-nitro-, 1-oxide (CAS 13602-73-8); 2-pyridinol, 4-chloro-, 1-oxide (CAS 13602-65-8); 2-pyridinol, 4-nitro-, 1-oxide (CAS 13602-63-6); and 2-pyridinol, 4-methyl-, 1-oxide (CAS 1952-64-3), and mixtures thereof. These materials are commercially available from, for example, Sigma-Aldrich (St. Louis, Mo.) and/or Aces Pharma (Branford, Conn.).

In certain aspects, the 2-pyridinol-N-oxide material is a 2-pyridinol-N-oxide material selected from the group consisting of: 2-hydroxypyridine-1-oxide; 3-pyridinecarboxylic acid, 2-hydroxy-, 1-oxide; 6-hydroxy-3-pyridinecarboxylic acid, 1-oxide; 2-hydroxy-4-pyridinecarboxylic acid, 1-oxide; 2-pyridinecarboxylic acid, 6-hydroxy-, 1-oxide; 6-hydroxy-3-pyridinesulfonic acid, 1-oxide; and mixtures thereof.

In certain aspects, the 2-pyridinol-N-oxide material is a 1-Hydroxy-2(1H)-pyridinone material selected from the group consisting of: 1-Hydroxy-2(1H)-pyridinone (CAS 822-89-9); 1,6-dihydro-1-hydroxy-6-oxo-3-Pyridinecarboxylic acid (CAS 677763-18-7); 1,2-dihydro-1-hydroxy-2-oxo-4-Pyridinecarboxylic acid (CAS 119736-22-0); 1,6-dihydro-1-hydroxy-6-oxo-2-Pyridinecarboxylic acid (CAS 94781-89-2); 1-hydroxy-4-methyl-6-(2,4,4-trimethylpentyl)-2(1H)-Pyridinone (CAS 50650-76-5); 6-(cyclohexylmethyl)-1-hydroxy-4-methyl-2 (1H)-Pyridinone (CAS 29342-10-7); 1-hydroxy-4,6-dimethyl-2(1H)-Pyridinone (CAS 29342-02-7); 1-Hydroxy-4-methyl-6-(2,4,4-trimethylpentyl)-2-pyridone monoethanolamine (CAS 68890-66-4); 1-hydroxy-6-(octyloxy)-2(1H)-Pyridinone (CAS 162912-64-3); 1-Hydroxy-4-methyl-6-cyclohexyl-2-pyridinone ethanolamine salt (CAS 41621-49-2); 1-Hydroxy-4-methyl-6-cyclohexyl-2-pyridinone (CAS 29342-05-0); 6-ethoxy-1,2-dihydro-1-hydroxy-2-oxo-4-Pyridinecarboxylic acid, methyl ester (CAS 36979-78-9); 1-hydroxy-5-nitro-2(1H)-Pyridinone (CAS 45939-70-6); and mixtures thereof. These materials are commercially available from, for example, Sigma-Aldrich (St. Louis, Mo.), Princeton Building Blocks (Monmouth Junction, N.J.), 3B Scientific Corporation (Libertyville, Ill.), SynFine Research (Richmond Hill, ON), Ryan Scientific, Inc. (Mt. Pleasant, S.C.), and/or Aces Pharma (Branford, Conn.).

In certain aspects, the 2-pyridinol-N-oxide material is a 2-pyridinol-N-oxide material or tautomer thereof according to the formula(s) below:

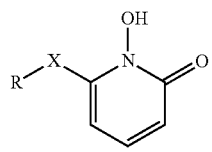

where X is an oxygen or sulfur moiety and R is a substituted or unsubstituted hydrocarbon group having between 1 and 20 carbon atoms. Materials of this class can be synthesized following the procedure disclosed in U.S. Pat. No. 5,675,013.

In certain aspects, the 2-pyridinol-N-oxide material is a 2-pyridinol-N-oxide material or tautomer thereof according to the formula(s) below:

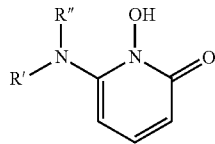

Wherein R' and R" are independently either hydrogen or a substituted or unsubstituted hydrocarbon group having between 1 and 20 carbon atoms. Materials of this class can be synthesized following the procedure disclosed in U.S. Pat. No. 5,675,013. In certain aspects, the 2-pyridinol-N-oxide material is 1-Hydroxy-4-methyl-6-(2,4,4-trimethylpentyl)-2-pyridone monoethanolamine salt.

In the present invention, the hair care composition may contain from about 0.1% to about 10% of a substituted or unsubstituted 2-pyridinol N-oxide material. Alternatively, the hair care composition may contain from about 0.3% to about 3% of a substituted or unsubstituted 2-pyridinol N-oxide material. Alternatively, the hair care composition may contain from about 0.5% to about 2% of a substituted or unsubstituted 2-pyridinol N-oxide material.

Ratio Discussion

In the present invention, the ratio of a polyvalent metal salt of pyrithione to a 2-pyridinal-N-oxide for achieving synergistic antioxidant activity may be from about 0.5 to about 1.5, in combination with the ratio of a 2-pyridinal-N-oxide to a zinc containing layered material is from about 0.2 to about 1.0 and further in combination with a ratio of a polyvalent metal salt of pyrithione to a zinc containing layered material of from about 0.2 to about 1.0. Further, the ratio of the ratio of a polyvalent metal salt of pyrithione to a 2-pyridinal-N-oxide for achieving synergistic antioxidant activity may be from about 0.7 to about 1.3, in combination with the ratio of a 2-pyridinal-N-oxide to a zinc containing layered material is from about 0.4 to about 0.9 and further in combination with a ratio of a polyvalent metal salt of pyrithione to a zinc containing layered material of from about 0.4 to about 0.9.

Methods

Peroxide-Induced Keratinocyte Stress

Figure 5:
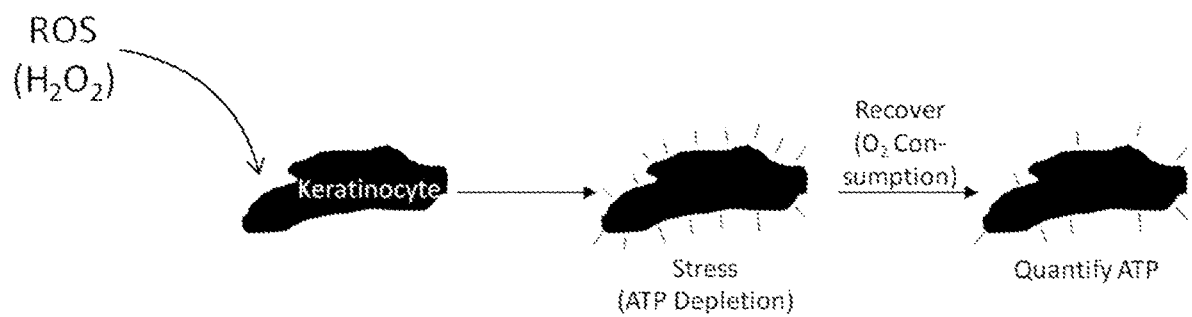
FIG. 5. This is a schematic of Peroxide-Induced Keratinocyte Stress.

The principle used in this in vitro cellular methodology is oxidatively stress keratinocytes, which depletes their cellular energy (ATP) and then to quantify the ability of various materials to inhibit the negative consequences of the oxidative stress (higher ATP is more effective) as demonstrated in FIG. 5.

This methodology is further discussed in Assessing bioenergetic function in response to oxidative stress by metabolic profiling. Free Radical Biology and Medicine; Dranka B P, Benavides G A, Diers A R, Giordano S, Zelickson B R, Reily C, Zou L, Chatham J C, Hill B G, Zhang J, Landar A; 2011 Nov. 1; 51(9):1621-35, incorporated herein by reference, as well as in Proceedings of the National Academy of Sciences of the United States of America; Miyoshi N, Oubrahim H, Chock P B, Stadtman E R . . . 2006 Feb. 7; 103(6):1727-31, incorporated herein by reference.

Experimental Methodology: This method demonstrates the synergistic reduction in Adenosine Triphosphate (ATP) depletion caused by Reactive Oxygen Species (ROS). Hydrogen peroxide is a well-known ROS as is commonly used as a surrogate to analyze the effects of a variety of ROS. In this test, keratinocytes are cultured (passage <8) in T150 flasks using Epi-Life medium (Calcium Free and Phenol Red Free, supplemented with penicillin/streptomycin and keratinocytes growth supplement, Invitrogen cat #MEPICF-PRF500) in a CO2 incubator (Forma 51030532, Marietta Ohio). The keratinocytes are then plated into 96 well plates, 10,000 cells/well, 0.2 ml media. After 24 hours incubation in 37° C. in CO2 Incubator, the keratinocytes are treated with 500 uM hydrogen peroxide alone and with 0.0000061 w/v % of zinc pyrithione, 0.0000061 w/v % of piroctone olamine, 0.0000097 w/v % of zinc carbonate individually and all together in combination for 1 hour. The keratinocytes are washed in PBS and ATP levels are measured using the Cell Titer-Glo® system (Promega cat #G7571/2/3, Madison, Wis.) per manufacturer's directions. Luminescence is measured on a SpectraMax $M^3$ (Molecular Devices, Sunnyvale, Calif.). Net luminescence is calculated by subtracting the luminescence counts from the vehicle control from the luminescence counts from the treatment groups. Synergy is defined by the observed luminescence value from the triple combination exceeding (with p-value <0.05) the sum of luminescence values of each individual component.

Results:

As demonstrated in FIG. 1, the results upon application of this method are shown and demonstrate a statistically significant (p=0.0003) synergistic level of activity for the triad over the calculated sum of individual observations.

Ascorbic Acid Oxidation Assay

The principle behind this chemical methodology is that iron can catalyze the oxidation of ascorbic acid, which can be followed spectrophotometrically by loss of UV absorbance due to ascorbic acid:

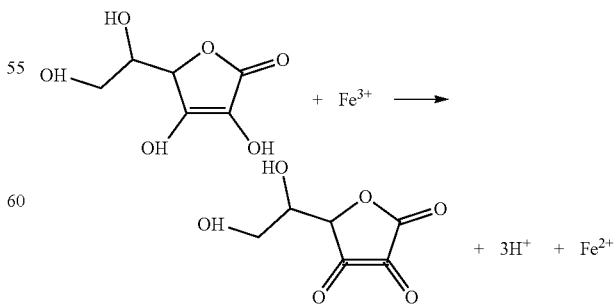

This methodology is further discussed in: The action of nine chelators on iron-dependent radical damage; R. T. Dean and P. Nicholson (1994). *Free Rad. Res.*, Vol 20, No. 2, pp. 83-101, incorporated herein by reference, and further in Examination of the antiproliferative activity of iron chelators: multiple cellular targets and the different mechanism of action of triapine compared with desferrioxamine and the potent pyridoxal isonicotinoyl hydrazone analogue 311;[1] Chaston T., Lovejoy B., Watts R., and D. R. Richardson (2003). *Clinical Cancer Research* Vol. 9 402-414, incorporated herein by reference; and further in: In the absence of catalytic metals ascorbate does not autoxidize at pH 7: ascorbate as a test for catalytic metals G. R. Buettner (1988); *Journal of Biochemical and Biophysical Methods*, 16 27-40, incorporated herein by reference.

Experimental Methodology: Metal-free water is prepared by treating Millipore water with Chelex 100 Resin (Sigma-Aldrich, St. Louis, Mo.). All antioxidants tested in the study are prepared in DMSO (Millipore, Burlington, Mass.). Due to the low solubility of $ZnCO_3$ (Sigma-Aldrich, St. Louis, Mo.) in DMSO, $ZnCO_3$ supernatant is used for the assay. Ascorbate oxidation assay is done in a 96-well quartz plate. The assay consists of 3 mM Sodium phosphate solution (Sigma-Aldrich, St. Louis, Mo.) (pH-7), antioxidants, DMSO, 200 µM $FeCl_3$ (Sigma-Aldrich, St. Louis, Mo.) and 200 µM ascorbic acid (Sigma-Aldrich, St. Louis, Mo.). Five conditions including DMSO blankS, 19.2 µM $ZnCO_3$, 12 µM piroctone olamine, 12 µM ZPT and combination of $ZnCO_3$, piroctone olamine, ZPT (19.2 µM, 12 µM, 12 µM, respectively) are tested in 6 replicates. Ascorbic acid is freshly prepared each time right before use. Absorbance at 265 nm is recorded by a SpectraMax M5 plate reader (Molecular Devices, San Jose, Calif.) at 1 min and 24 hr. Ascorbic acid absorbs at 265 nm. Absorbance decreases when ascorbic acid is oxidized. The absorbance decrease is converted to % inhibition relative to a DMSO blank which represented maximum oxidation.

Figure 2:
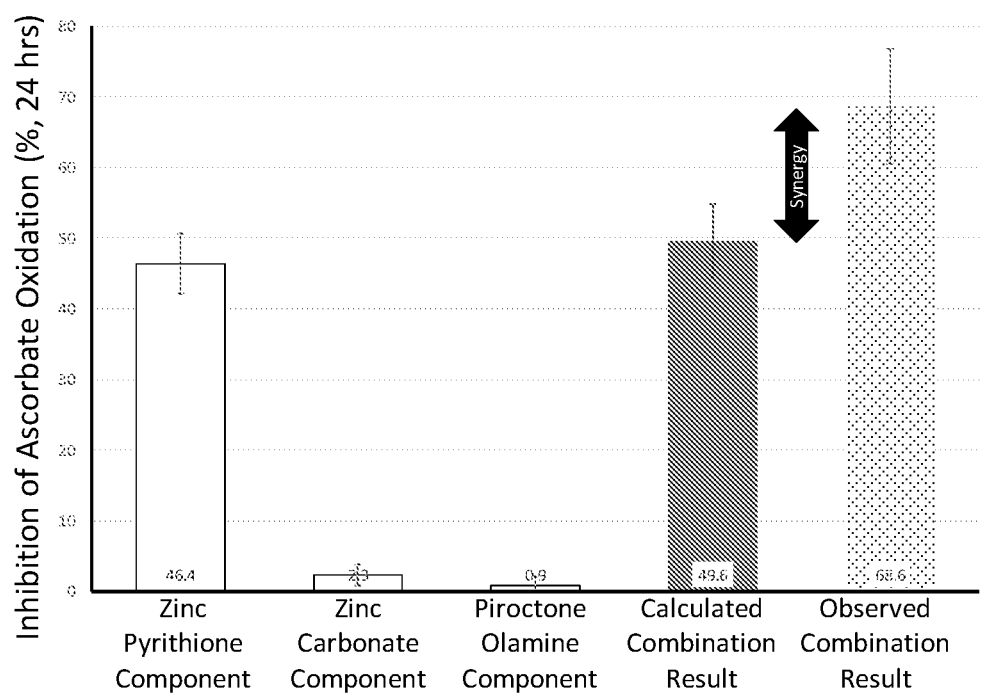
FIG. 2 depicts an Ascorbic Acid Oxidation assay demonstrating a statistically significant (p=0.01) larger triad activity than the calculated additive effect of the combination

Results:

As demonstrated in FIG. 2, this methodology also shows a statistically significant (p=0.01) larger triad activity than the calculated additive effect of the combination.

Ferric Ion Reducing Antioxidant Parameter, FRAP

A common anti-oxidant activity screening assay involves inhibiting the oxidation of an iron complex and its concomitant change in color:

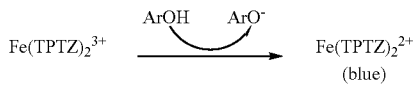

This methodology is further discussed in: "The ferric reducing ability of plasma (FRAP) as a measure of "antioxidant power"; Benzie, Iris F F, and J. J. Strain.: the FRAP assay." Analytical biochemistry 239.1 (1996): 70-76. Analytical biochemistry 239.1 (1996): 70-76, incorporated herein by reference.

Experimental Methodology: The Ferric Reducing Antioxidant Power (FRAP) method is a quantitative assay for measuring the antioxidant potential in food. The rationale behind this assay is that electron donating reducing power of antioxidants could reduce Fe3+ into Fe2+, which further reacts with a colorimetric probe to produce a blue product. Absorbance at 593 nm is measured and results are expressed as micromole Trolox equivalency per gram of a tested material. Samples are weighed and mixed with 1:1 (v/v) acetone and water and are vortexed for 30 seconds, followed by extraction on orbital shaker (1 hour at room temperature).

Then, mixture is centrifuged at 800×g for 10 min at room temperature and the resulting supernatant is used for assay performance with proper dilution. Kinetic absorbance profile is detected using Biotek plate reader with absorbance at 593 nm, at 37° C. From obtained experimental data, net absorbance is calculated by subtracting absorbance of the blank from AUC of sample/standard. The relative FRAP value (expressed as Trolox equivalent) is calculated by extrapolation from Trolox calibration curve. FRAP value of sample is reported as mean value.

Figure 3:
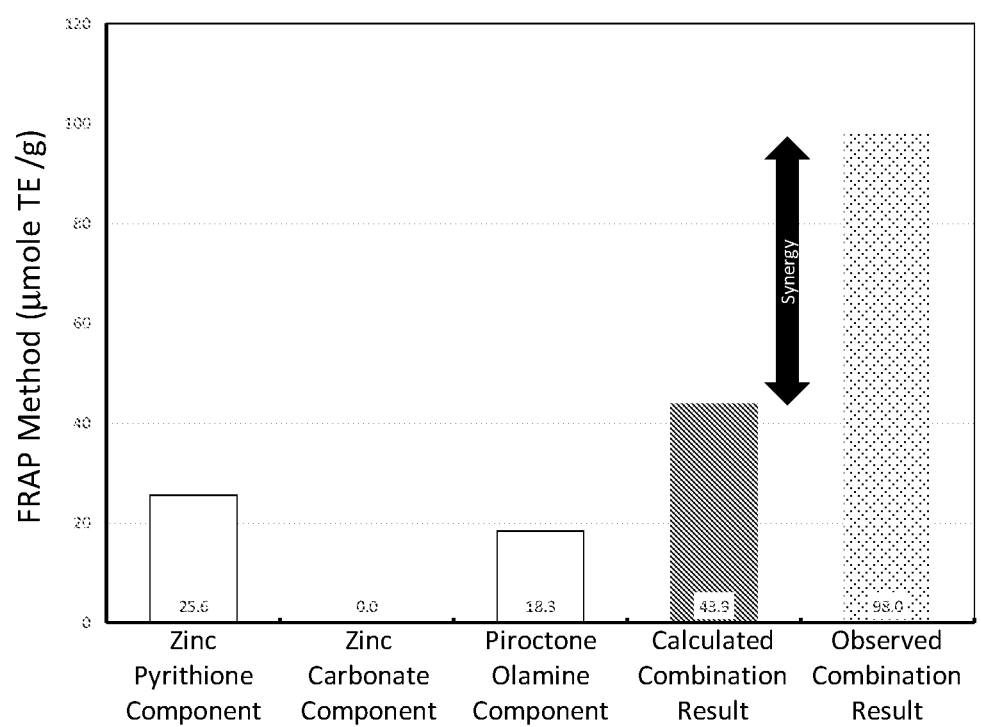
FIG. 3 depicts a Ferric Ion Reducing Antioxidant Parameter assay demonstrating a strong synergy for the triad combination over the calculated additive result.

Results: As demonstrated in FIG. 3, this commonly used antioxidant assay clearly demonstrates a strong synergy for the triad combination over the calculated additive result.

Oxygen Radical Absorbance Capacity (ORAC) Peroxynitrite Assay

The ORAC assay is the most common method for assessing antioxidant activity. It is based on evaluating the capacity of a test material to protect a probe (e.g., a chromagen) from its damage by oxygen radicals (in this case, peroxynitrite). Results are expressed as micromole Trolox Equivalency per gram of the test material:

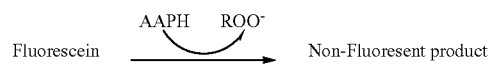

This methodology is further discussed in: "Development and validation of an improved oxygen radical absorbance capacity assay using fluorescein as the fluorescent probe."; Ou, Boxin, Maureen Hampsch-Woodill, and Ronald L. Prior. *Journal of agricultural and food chemistry* 49.10 (2001): 4619-4626 incorporated herein by reference; and further in "Development and validation of oxygen radical absorbance capacity assay for lipophilic antioxidants using randomly methylated β-cyclodextrin as the solubility enhancer.", Huang, Dejian, et al. *Journal of Agricultural and Food Chemistry* 50.7 (2002): 1815-1821, incorporated herein by reference.

Experimental Methodology: The ORAC Peroxynitrite measures the peroxynitrite radical. In this assay, 3-morpholinosyndnonimine hydrochloride (SIN-1) is used as the source for the peroxynitrite radical, which is generated as a result of the spontaneous decomposition of SIN-1 at 37° C. Dihydrorhodamine-123 is the chosen target protein, whose loss of fluorescence (with excitation at 485 nm and emission at 528 nm) is an indication of the extent of damage from its reaction with the peroxynitrite radical. The protective effect of the antioxidants is measured by assessing the IC50 of the samples versus Trolox, which is used as the calibration standard. Samples are weighed and mixed with 1:1 (v/v) acetone and water and are vortexed for 30 seconds, followed by extraction on orbital shaker (1 hour at room temperature). Then, mixture is centrifuged at 800×g for 10 min at room temperature and the resulting supernatant is used for assay performance with proper dilution. Kinetic fluorescence profile is detected using Biotek plate reader with excitation at 485 nm and emission at 528 nm, at 37° C. From obtained experimental data, the relative ORAC value (expressed as Trolox equivalent) is calculated by IC50 of Trolox over IC50 of sample. ORAC value of sample is reported as mean value.

Figure 4:
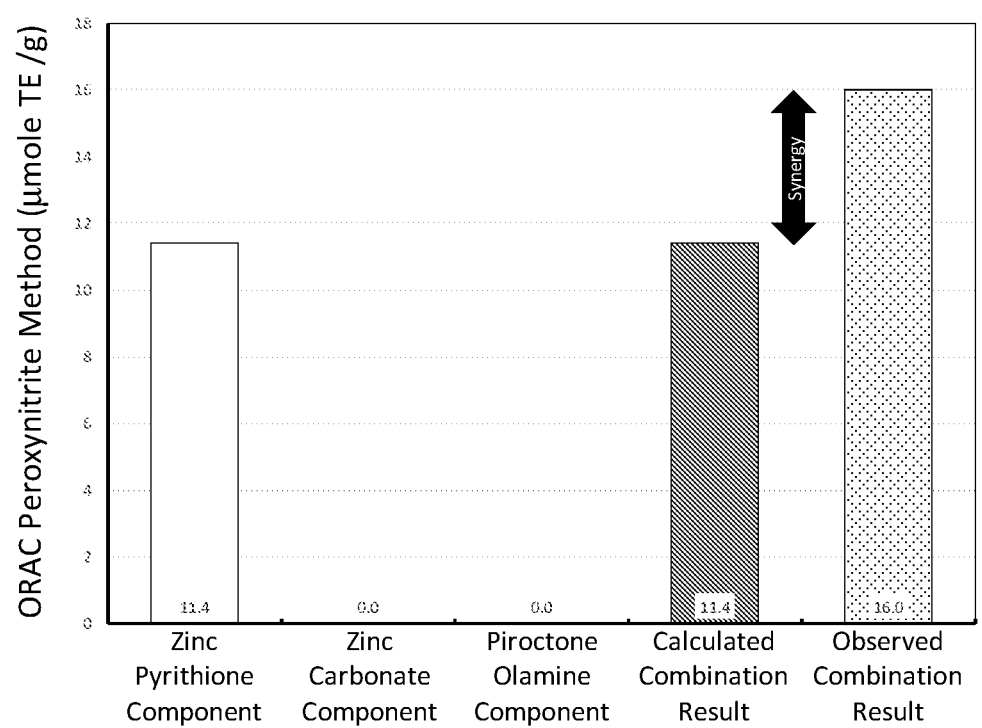
FIG. 4 depicts an Oxygen Radical Absorbance Capacity (ORAC) Peroxynitrite assay demonstrating ZPT is the only individual material that showed appreciable activity, yet the triad demonstrated a higher antioxidant activity indicating synergism.

Results:

As demonstrated in FIG. 4, ZPT is the only individual material that showed appreciable activity, yet the triad demonstrated a higher antioxidant activity indicating synergism.

HODE is used as a representative biomarker of the level of oxidative stress being experienced by either the scalp or hair (Spiteller, P. and G. Spiteller 9-Hydroxy-10,12-octadecadienoic acid (9-HODE) and 13-hydroxy-9,11-octadecadienoic acid (13-HODE): excellent markers for lipid peroxidation Chem Phys Lipids 1997, 89, 131-9. In all cases, the level of HODE is expressed as a ratio (normalized) to separately measured levels of parent linoleic acid from the same sample. Results are expressed as either the logarithm of the absolute level or, for treatment data, the percent reduction in the ratio as compared to baseline. Measures and Method: The measures of scalp and hair health are related to quantification of the degree of oxidative stress. Exemplified herein is the quantitation of (±)-9-hydroxy-10E, 12Z-octadecadienoic acid and (±)-13-hydroxy-10E, 12Z-octadecadienoic acid ("HODE"). Quantitation of oxidized lipids from extracts of the adhesive article, tape strips, can be conducted using gradient reversed-phase high performance liquid chromatography with tandem mass spectrometry (HPLC/MS/MS).

Tape strips (single or multiple tape strips) obtained from the scalp of human subjects are placed into individual polypropylene amber vials or glass amber vials, and then extracted with extraction solvent (methanol with 0.1% butylated hydroxytoluene, w/v) using vortexing for 10 min. Hair samples from the head are simultaneously pulverized and extracted using the extraction solvent in a bead-based device. The standards and the extracts of the scalp tape strips and hair extracts are analyzed using gradient reversed-phase high performance liquid chromatography with tandem mass spectrometry (HPLC/MS/MS). Analytes (oxidized or non-oxidized lipids) and the ISTDs are monitored by positive ion electrospray (ESI). A standard curve is constructed by plotting the signal, defined here as the peak area ratio (peak area analyte/peak area ISTD) or peak area analyte only, for each standard versus the mass of each analyte for the corresponding standard. The mass of each analyte in the calibration standards and human scalp extract samples are then back-calculated using the generated regression equation. The result can be reported as the mass of oxidized lipid/tape strip or the result can be standardized by dividing by the amount of oxidized lipid by the amount of the corresponding parent non-oxidized lipid that is also found in the tape strip extract. Additionally, results could be reported by standardizing the amount of oxidized lipid by the amount of corresponding protein found in the tape strip extract. Standardization could also be done by collecting the cells removed, drying them and weighing them.

In the present invention, there may be a method of using a composition comprising a polyvalent metal salt of pyrithione; a 2-pyridinol-N-oxide material; a zinc containing layered material; wherein the ratio of a:b is from about 0.5 to about 1.5; the ratio of b:c is about 0.2 to about 1.0; and the ratio of a:c is about 0.2 to about 1.0 to provide a synergistic antioxidant activity wherein there is at least about a 10% reduction in (±)-9-hydroxy-10E, 12Z-octadecadienoicacid and (±)-13-hydroxy-10E, 12Z-octadecadienoic acid (HODE) on a scalp compared to a baseline HODE; of at least about a 15% reduction in (±)-9-hydroxy-10E, 12Z-octadecadienoicacid and (±)-13-hydroxy-10E, 12Z-octadecadienoic acid (HODE) on a scalp compared to a baseline HODE; of at least about a 20% reduction in (±)-9-hydroxy-10E, 12Z-octadecadienoicacid and (±)-13-hydroxy-10E, 12Z-octadecadienoic acid (HODE) on a scalp compared to a baseline HODE; and of at least about a 25% octadecadienoic acid (HODE) on a scalp compared to a baseline HODE.

Detersive Surfactant

The present invention may be present in the form of a shampoo, conditioner, or leave on treatment. The shampoo composition may comprise one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. The anionic surfactant may be sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Further, zwitterionics such as betaines may be selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Conditioner Composition

The conditioner composition described herein comprises (i) from about 0.025% to about 0.25%, alternatively from about 0.05% to about 0.2%, alternatively from about 0.1% to about 0.15% histidine, by weight of the conditioner composition, and (ii) a conditioner gel matrix. After applying to the hair a conditioner composition as described herein, the method then comprises rinsing the conditioner composition from the hair. The conditioner composition also comprises a conditioner gel matrix comprising (1) one or more high melting point fatty compounds, (2) a cationic surfactant system, and (3) a second aqueous carrier.

A. Cationic Surfactant System

The conditioner gel matrix of the conditioner composition includes a cationic surfactant system. The cationic surfactant system can be one cationic surfactant or a mixture of two or more cationic surfactants. The cationic surfactant system can be selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amidoamine salt and mono-long alkyl quaternized ammonium salt.

The cationic surfactant system can be included in the composition at a level by weight of from about 0.1% to about 10%, from about 0.5% to about 8%, from about 0.8% to about 5%, and from about 1.0% to about 4%.

Mono-Long Alkyl Quaternized Ammonium Salt

The monoalkyl quaternized ammonium salt cationic surfactants useful herein are those having one long alkyl chain which has about 22 carbon atoms and may be a C22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula

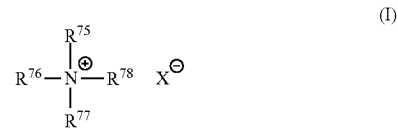

(I)

wherein one of $R^{75}$, $R^{76}$, $R^{77}$ and $R^{78}$ is selected from an alkyl group of 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of about 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of about 22 carbons. Exemplary tertiary amido amines include: behenamidopropyldimethylamine, behenamidopropyldiethylamine, behenamidoethyldiethylamine, behenamidoethyldimethylamin. Useful amines in the present invention are disclosed in U.S. Pat. No. 4,275,055, Nachtigal, et al. These amines can also be used in combination with acids such as ℓ-glutamic acid, lactic acid, hydrochloric acid, malic acid, succinic acid, acetic acid, fumaric acid, tartaric acid, citric acid, ℓ-glutamic hydrochloride, maleic acid, and mixtures thereof; further, may be ℓ-glutamic acid, lactic acid, and/or citric acid. The amines herein can be partially neutralized with any of the acids at a molar ratio of the amine to the acid of from about 1:0.3 to about 1:2, and/or from about 1:0.4 to about 1:1.

Di-Long Alkyl Quaternized Ammonium Salt

Di-long alkyl quaternized ammonium salt can be combined with a mono-long alkyl quaternized ammonium salt or mono-long alkyl amidoamine salt. It is believed that such combination can provide easy-to rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of from about 10% to about 50%, and/or from about 30% to about 45%.

The di-long alkyl quaternized ammonium salt cationic surfactants useful herein are those having two long alkyl chains having about 22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

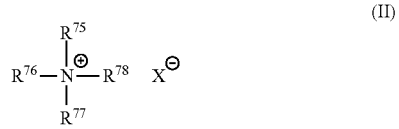

(II)

wherein two of $R^{75}$, $R^{76}$, $R^{77}$ and $R^{78}$ is selected from an alkyl group of from 22 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 22 carbons, or higher, can be saturated or unsaturated. One of $R^{75}$, $R^{76}$, $R^{77}$ and $R^{78}$ can be selected from an alkyl group of from 22 carbon atoms, the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Such dialkyl quaternized ammonium salt cationic surfactants include, for example, dialkyl ($C_{22}$) dimethyl ammonium chloride, ditallow alkyl dimethyl ammonium chloride, dihydrogenated tallow alkyl dimethyl ammonium chloride. Such dialkyl quaternized ammonium salt cationic surfactants also include, for example, asymmetric dialkyl quaternized ammonium salt cationic surfactants.

B. High Melting Point Fatty Compound

The conditioner gel matrix of the conditioner composition includes one or more high melting point fatty compounds. The high melting point fatty compounds useful herein may have a melting point of 25° C. or higher, and is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are suitable for use in the conditioner composition. The fatty alcohols useful herein are those having from about 14 to about 30 carbon atoms, from about 16 to about 22 carbon atoms. These fatty alcohols are saturated and can be straight or branched chain alcohols. Suitable fatty alcohols include, for example, cetyl alcohol, stearyl alcohol, behenyl alcohol, and mixtures thereof.

High melting point fatty compounds of a single compound of high purity can be used. Single compounds of pure fatty alcohols selected from the group of pure cetyl alcohol, stearyl alcohol, and behenyl alcohol can also be used. By "pure" herein, what is meant is that the compound has a purity of at least about 90%, and/or at least about 95%. These single compounds of high purity provide good rims ability from the hair when the consumer rinses off the composition.

The high melting point fatty compound can be included in the conditioner composition at a level of from about 0.1% to about 20%, alternatively from about 1% to about 15%, and alternatively from about 1.5% to about 8% by weight of the composition, in view of providing improved conditioning benefits such as slippery feel during the application to wet hair, softness and moisturized feel on dry hair.

C. Aqueous Carrier

The conditioner gel matrix of the conditioner composition includes a second aqueous carrier. Accordingly, the formulations of the conditioner composition can be in the form of pourable liquids (under ambient conditions). Such compositions will therefore typically comprise a second aqueous carrier, which is present at a level of from about 20 wt % to about 95 wt %, or from about 60 wt % to about 85 wt %. The second aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The second aqueous carriers useful in the conditioner composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

Additional Components

The shampoo composition, conditioner compositions, and/or leave-on treatments described herein may optionally comprise one or more additional components known for use in hair care or personal care products, provided that the additional components are physically and chemically compatible with the essential components described herein, or do not otherwise unduly impair product stability, aesthetics or performance. Such additional components are most typically those described in reference books such as the CTFA Cosmetic Ingredient Handbook, Second Edition, The Cosmetic, Toiletries, and Fragrance Association, Inc. 1988, 1992. Individual concentrations of such additional components may range from about 0.001 wt % to about 10 wt % by weight of the hair care compositions.

Non-limiting examples of additional components for use in the hair care compositions include conditioning agents, natural cationic deposition polymers, synthetic cationic deposition polymers, anti-dandruff agents, particles, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, proteins, skin active agents, sunscreens, UV absorbers, and vitamins.

1. Conditioning Agent

The hair care compositions may comprise one or more conditioning agents. Conditioning agents include materials that are used to give a particular conditioning benefit to hair. The conditioning agents useful in the hair care compositions of the present invention typically comprise a water-insoluble, water-dispersible, non-volatile, liquid that forms emulsified, liquid particles. Suitable conditioning agents for use in the hair care composition are those conditioning agents characterized generally as silicones, organic conditioning oils or combinations thereof, or those conditioning agents which otherwise form liquid, dispersed particles in the aqueous surfactant matrix.

One or more conditioning agents are present from about 0.01 wt % to about 10 wt %, from about 0.1 wt % to about 8 wt %, and from about 0.2 wt % to about 4 wt %, by weight of the composition.

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers Organic Conditioning Materials The conditioning agent of the compositions of the present invention may also comprise at least one organic conditioning material such as oil or wax, either alone or in combination with other conditioning agents, such as the silicones described above. The organic material can be nonpolymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-20 200, PEG-400, PEG-600, PEG-1000, PEG-2M, PEG-7M, PEG-14M, PEG-45M and mixtures thereof.

Benefit Agents

The hair care composition may further comprise one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, perfumes, brighteners, enzymes, sensates, attractants, dyes, pigments, bleaches, and mixtures thereof.

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, and treatment products; and any other form that may be applied to hair.

The hair care compositions are generally prepared by conventional methods such as are known in the art of making the compositions. Such methods typically involve mixing of the ingredients in one or more steps to a relatively uniform state, with or without heating, cooling, application of vacuum, and the like. The compositions are prepared such as to optimize stability (physical stability, chemical stability, photostability) and/or delivery of the active materials. The hair care composition may be in a single phase or a single product, or the hair care composition may be in a separate phases or separate products. If two products are used, the products may be used together, at the same time or sequentially. Sequential use may occur in a short period of time, such as immediately after the use of one product, or it may occur over a period of hours or days.

EXAMPLES

Non-Limiting Examples

The shampoo compositions illustrated in the following examples are prepared by conventional formulation and mixing methods. All exemplified amounts are listed as weight percents on an active basis and exclude minor materials such as diluents, preservatives, color solutions, imagery ingredients, botanicals, and so forth, unless otherwise specified. All percentages are based on weight unless otherwise specified.

| Component | Example | | | | | |
| --- | --- | --- | --- | --- | --- | --- |
| | 1 | 2 | 3 | 4 | 5 | 6 |
| Guar hydroxypropyltrimonium chloride 1 | 0.3 | 0.3 | 0.3 | 0.25 | 0.3 | 0.3 |

-continued

| | | | | | | |
|---|---|---|---|---|---|---|
| Acrylamide/Triquat 2 | — | — | — | — | — | 0.03 |
| Sodium laureth-1 sulfate 3 | 12 | 12 | 12.5 | 12 | 12 | 11.5 |
| Sodium Lauryl sulphate 4 | 0 | 0 | — | — | — | 1.5 |
| Cocamidopropyl betaine 5 | 1.5 | 1.5 | 1.5 | 1.5 | — | 1.25 |
| Cocamide MEA 6 | 1.5 | 1.5 | 1.5 | 1.5 | 1.5 | 2 |
| Dimethicone 7 | 2.7 | 0.8 | 0.8 | 0.85 | — | 0.8 |
| Dimethiconol 8 | — | — | — | — | 1 | — |
| Zinc Pyrithione 9 | 1 | 1 | 1 | 1 | 1 | 1 |
| Zinc Carbonate 10 | 1.61 | 1.61 | 1.61 | 1.61 | 1.61 | 1.61 |
| Stearyl Alcohol 11 | — | — | — | — | 1.29 | — |
| Cetyl Alcohol 12 | — | — | — | — | 0.71 | — |
| Glycol distearate 13 | 1.5 | 1.5 | 1.5 | 1.5 | 1.5 | 1.5 |
| Preservative 14 | 0.05 | 0.05 | 0.05 | 0.05 | 0.05 | 0.05 |
| Piroctone Olamine 15 | 1 | 1 | 1 | 1 | 1 | 1 |
| Caffeine 16 | 0.1 | 0.1 | 0.1 | 0.1 | 0.1 | — |
| Niacinamide 17 | 0.005 | 0.005 | — | — | 0.005 | — |
| Panthenol 18 | 0.005 | 0.005 | — | — | 0.005 | — |
| Polyquaternium-10 19 | 0.2 | 0.1 | 0.2 | 0.1 | 0.1 | — |
| Sodium Xylene Sulfonate 20 | QS | QS | QS | QS | QS | QS |
| Fragrance | 0.9 | 0.9 | 0.9 | 0.9 | 0.9 | 0.8 |
| Hydrochloric Acid 6N | QS | QS | QS | QS | QS | QS |
| Sodium Benzoate | 0.25 | 0.25 | 0.25 | 0.25 | 0.25 | 0.25 |
| Sodium Chloride | QS | QS | QS | QS | QS | QS |
| Water | 75.38 | 77.38 | 76.79 | 77.39 | 76.68 | 76.41 |
| Total | 100 | 100 | 100 | 100 | 100 | 100 |

1. Jaguar C500 from Solvay with a M. Wt. of about 500,000 g/mol and charge density of about 0.8 meq/g.
2. Polyquaternium-76 (PQ-76) from Rhodia with a M. Wt. of about 1,000,000 g/mol and charge density of about 1.6 meq/g.
3. Sodium laureth-1 sulfate at 26% active from the Stepan Company
4. Sodium Lauryl sulfate at 29% active from the Stepan Company
5. Amphosol HCA at 30% active from the Stepan Company
6. Ninol COMF at 85% active from the Stepan Company
7. Viscasil 330M from Momentive Performance Materials with a viscosity of 330,000 cSt (centistokes) utilizing about an average 30 micron emulsion.
8. BELSIL DM 5500 from Wacker Silicones
9. ZPT from Arch Chemical
10. Zinc carbonate from the Bruggeman Group
11. CO-1895 from Procter & Gamble
12. CO-1695 from Procter & Gamble
13. EGDS from Golschmidt Chemical Company
14. Kathon CG from Akzo Nobel
15. Octopirox from Clairiant
16. BASF Beauty Care Solutions
17. Roche Vitamins Inc
18. DSM Nutritional Products (Ayrshire GB)
19. JR30M available from Dow/Amerchol -
20. Stepanate SXS at 40% from Stepan The following examples further describe and demonstrate non-limiting within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Conditioner Examples

| Components | Ex. 7 | Ex. 8 | Ex. 9 | Ex. 10 | Ex. 11 |
|---|---|---|---|---|---|
| Zinc pyrithione *1 | 0.75 | 0.75 | 0.75 | 0.75 | 0.5 |
| Zinc carbonate *2 | 1.2 | 1.2 | 1.2 | 1.2 | 0.8 |
| Piroctone Olamine *3 | 0.75 | 0.75 | 0.75 | 0.75 | 0.5 |
| Behenyl trimethyl ammonium chloride | — | — | — | 2.5 | 0.9 |
| Behenyl trimethyl ammonium methosulfate | 2.6 | 2.6 | 1.2 | — | — |
| Dicetyl dimethyl ammonium chloride | — | — | 0.35 | — | — |
| Cetyl alcohol | 1.0 | 1.0 | 1.0 | 1.0 | 1.0 |
| Stearyl alcohol | 2.4 | 2.4 | 2.3 | 2.3 | 2.3 |
| Aminosilicone *4 | 0.5 | 0.5 | 0.5 | 0.5 | 0.5 |
| Preservatives | 0.9 | 0.9 | 0.9 | 0.9 | 0.9 |
| Perfume | 0.5 | 0.5 | 0.5 | 0.5 | 0.5 |
| Panthenol | — | — | — | 0.05 | — |
| Panthenyl ethyl ether | — | — | — | — | 0.03 |
| Deionized Water | q.s. to 100% | | | | |

Definitions of Components
*1 Zinc pyrithione: having a particle size of from about 1 to about 10 microns
*2 Zinc carbonate: having a particle size of from about 1 to about 10 microns
*3 Octopirox from Clairiant
*4 Aminosilicone: Terminal aminosilicone which is available from GE having a viscosity of about 10,000 mPa · s, and having following formula: $(R_1)_aG_{3-a}$-Si—(—O-SiG$_2$)$_n$-O—SiG$_{3-a}(R_1)_a$ wherein G is methyl; a is an integer of 1; n is a number from 400 to about 600; $R_1$ is a monovalent radical conforming to the general formula $C_qH_{2q}L$, wherein q is an integer of 3 and L is —NH$_2$.

Product Form

The hair care compositions of the present invention may be presented in typical hair care formulations. They may be in the form of solutions, dispersion, emulsions, powders, talcs, encapsulated, spheres, spongers, solid dosage forms, foams, and other delivery mechanisms. The compositions of the present invention may be hair tonics, leave-on hair products such as treatment, and styling products, rinse-off hair products such as shampoos, pre-wash product, co-wash product, and personal cleansing products, and treatment products; and any other form that may be applied to hair.

Additional Examples/Combinations

A. A personal care composition comprising:
  a) a polyvalent metal salt of pyrithione;
  b) a 2-pyridinol-N-oxide material;
  c) a zinc containing layered material;
    wherein the ratio of a:b is from about 0.5 to about 1.5; the ratio of b:c is about 0.2 to about 1.0; and the ratio of a:c is about 0.2 to about 1.0 and wherein there is a synergistic antioxidant activity.
B. A personal care composition according to Paragraph A, wherein the synergistic antioxidant activity is at least 10% higher than the calculated sum of Claim 1a, 1b and 1c individual antioxidant activity.
C. A personal care composition according to Paragraph A-B, wherein the ratio of a:b is from about 0.7 to about 1.3.
D. A personal care composition according to Paragraph A-C, wherein the ratio of b:c is from about 0.4 to about 0.9.
E. A personal care composition according to Paragraph A-D, wherein the ratio of a:c is from about 0.4 to about 0.9.
F. A personal care composition according to Paragraph A-E, wherein the personal care composition is selected from group consisting of a shampoo, conditioner, leave-on, tonic and mixtures thereof.
G. A personal care composition according to Paragraph A-F, wherein the polyvalent metal salt of pyrithione is from about 0.5% to about 5%, by weight of the composition.
H. A personal care composition according to Paragraph A-G, wherein the polyvalent metal salt of pyrithione is from about 0.01% to about 5%, by weight of the composition.
I. A personal care composition according to Paragraph A-H, wherein the polyvalent metal salt (or 1-hydroxy-2-pyridinethione salt) is zinc pyrithione.
J. A personal care composition according to Paragraph A-I, wherein the 2-pyridinol-N-oxide material is from about 0.05% to about 5%, by weight of the composition.
K. A personal care composition according to Paragraph A-J, wherein the 2-pyridinol-N-oxide material is from about 0.3% to about 3%, by weight of the composition.
L. A personal care composition according to Paragraph A-K, wherein the 2-pyridinol-N-oxide material is selected from the group consisting of 1-Hydroxy-4-methyl-6-(2,4,4-monoethanolamine salt, 6-Cyclohexyl-1-hydroxy-4-methyl-2(1H)-pyridone ethanolammonium salt, 6-[[p-chlorophenoxy)phenoxy]methyl]-1 hydroxy-4-methyl-pyridone.
M. A personal care composition according to Paragraph A-L, wherein the zinc containing layered material is from about 0.01% to about 10%, by weight of the composition.
N. A personal care composition according to Paragraph A-M, wherein the zinc containing layered material is from about 0.1% to about 7%, by weight of the composition.
O. A personal care composition according to Paragraph A-N, wherein the zinc containing layered material is basic zinc carbonate.
P. A method of using a composition according to Paragraph A-O, comprising
  a) a polyvalent metal salt of pyrithione;
  b) a 2-pyridinol-N-oxide material;
  c) a zinc containing layered material;
    wherein the ratio of a:b is from about 0.5 to about 1.5; the ratio of b:c is about 0.2 to about 1.0; and the ratio of a:c is about 0.2 to about 1.0 to provide a synergistic antioxidant activity.
Q. A method of using a composition according to Paragraph A-P, comprising
  a) a polyvalent metal salt of pyrithione;
  b) a 2-pyridinol-N-oxide material;
  c) a zinc containing layered material;
    wherein the ratio of a:b is from about 0.5 to about 1.5; the ratio of b:c is about 0.2 to about 1.0; and the ratio of a:c is about 0.2 to about 1.0 to provide a synergistic antioxidant activity wherein there is at least about a 10% reduction in (±)-9-hydroxy-10E, 12Z-octadecadienoic acid and (±)-13-hydroxy-10E, 12Z-octadecadienoic acid (HODE) on a scalp compared to a baseline HODE.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a) a polyvalent metal salt of pyrithione;
   b) a 2-pyridinol-N-oxide material; and
   c) a zinc containing layered material;
   wherein the ratio of a:b is from about 0.5 to about 1.5; and the ratio of b:c is about 0.2 to about 1.0; and the ratio of a:c is about 0.2 to about 1.0 and wherein there is a synergistic antioxidant activity wherein the synergistic antioxidant activity is at least 10% higher than the calculated sum of 1 a, 1 b and 1 c individual antioxidant activity.

2. A personal care composition according to claim 1 wherein the ratio of a:b is from about 0.7 to about 1.3.

3. A personal care composition according to claim 1 wherein the ratio of b:c is from about 0.4 to about 0.9.

4. A personal care composition according to claim 1 and wherein the ratio of a:c is from about 0.4 to about 0.9.

5. A personal care composition according to claim 1 wherein the personal care composition is selected from group consisting of a shampoo, conditioner, leave-on, tonic and mixtures thereof.

6. A personal care composition according to claim 1 wherein the polyvalent metal salt of pyrithione is from about 0.01% to about 5%, by weight of the composition.

7. A personal care composition according to claim 6 wherein the polyvalent metal salt of pyrithione is from about 0.5% to about 5%, by weight of the composition.

8. A personal care composition according to claim 6 wherein the polyvalent metal salt (or a 1-hydroxy-2-pyridinethione salt) is zinc pyrithione.

9. A personal care composition according to claim 1 wherein the 2-pyridinol-N-oxide material is from about 0.05% to about 5%, by weight of the composition.

10. A personal care composition according to claim 9 wherein the 2-pyridinol-N-oxide material is from about 0.3% to about 3%, by weight of the composition.

11. A personal care composition according to claim 1 wherein the 2-pyridinol-N-oxide material is selected from the group consisting of 1-Hydroxy-4-methyl-6-(2,4,4-trimethylpentyl)-2-pyridone monoethanolamine salt, 6-Cyclohexyl-1-hydroxy-4-methyl-2(1H)-pyridone ethanolammonium salt, and 6-[[p-chlorophenoxy)phenoxy]methyl]-1 hydroxy-4-methyl-pyridone.

12. A personal care composition according to claim 1 wherein the zinc containing layered material is from about 0.01% to about 10%, by weight of the composition.

13. A personal care composition according to claim 12 wherein the zinc containing layered material is from about 0.1% to about 7%, by weight of the composition.

14. A personal care composition according to claim 12 wherein the zinc containing layered material is basic zinc carbonate.

15. A method of using a composition comprising:
   a) a polyvalent metal salt of pyrithione;
   b) a 2-pyridinol-N-oxide material; and
   c) a zinc containing layered material;
   wherein the ratio of a:b is from about 0.5 to about 1.5; the ratio of b:c is about 0.2 to about 1.0; and the ratio of a:c is about 0.2 to about 1.0 to provide a synergistic antioxidant activity wherein the synergistic antioxidant activity is at least 10% higher than the calculated sum of 1 a, 1 b and 1 c individual antioxidant activity wherein the composition is applied to hair.

16. A method of using a composition comprising:
   a) a polyvalent metal salt of pyrithione;
   b) a 2-pyridinol-N-oxide material; and
   c) a zinc containing layered material;
   wherein the ratio of a:b is from about 0.5 to about 1.5; the ratio of b:c is about 0.2 to about 1.0; and the ratio of a:c is about 0.2 to about 1.0 to provide a synergistic antioxidant activity wherein there is at least about a 10% reduction in (±)-9-hydroxy-10E, 12Z-octadecadienoic acid and (±)-13-hydroxy-10E, 12Z-octadecadienoic acid (HODE) on a scalp compared to a baseline HODE wherein the synergistic antioxidant activity is at least 10% higher than the calculated sum of 1 a, 1 b and 1 c individual antioxidant activity wherein the composition is applied to hair.

* * * * *